US009719940B2

(12) United States Patent
Manassen et al.

(10) Patent No.: US 9,719,940 B2
(45) Date of Patent: Aug. 1, 2017

(54) COMPRESSIVE SENSING WITH ILLUMINATION PATTERNING

(71) Applicant: KLA-TENCOR CORPORATION, Milpitas, CA (US)

(72) Inventors: Amnon Manassen, Haifa (IL); Andrew Hill, Berkeley, CA (US); Avi Abramov, Haifa (IL)

(73) Assignee: KLA—Tencor Corporation, Milpitas, CA (US)

(*) Notice: Subject to any disclaimer, the term of this patent is extended or adjusted under 35 U.S.C. 154(b) by 0 days.

(21) Appl. No.: 14/875,084

(22) Filed: Oct. 5, 2015

(65) Prior Publication Data

US 2016/0025646 A1    Jan. 28, 2016

Related U.S. Application Data

(63) Continuation of application No. PCT/US2015/021843, filed on Mar. 20, 2015.

(60) Provisional application No. 61/955,793, filed on Mar. 20, 2014.

(51) Int. Cl.
| | |
|---|---|
| *G01J 4/00* | (2006.01) |
| *G01N 21/88* | (2006.01) |
| *G01J 3/02* | (2006.01) |
| *G01N 21/956* | (2006.01) |
| *G03F 7/20* | (2006.01) |

(Continued)

(52) U.S. Cl.
CPC ............ *G01N 21/8806* (2013.01); *G01J 3/02* (2013.01); *G01N 21/47* (2013.01); *G01N 21/8851* (2013.01); *G01N 21/9501* (2013.01); *G01N 21/956* (2013.01); *G01N 21/95623* (2013.01); *G03F 7/70633* (2013.01); *G01N 2021/8848* (2013.01); *G01N 2201/06* (2013.01)

(58) Field of Classification Search
CPC ................. G01N 21/211; G01N 21/21; G01N 2021/213; G01J 4/00; G01B 11/0641
USPC ........................................................ 356/369
See application file for complete search history.

(56) References Cited

U.S. PATENT DOCUMENTS

| | | | |
|---|---|---|---|
| 2003/0161039 | A1 | 8/2003 | Fukano et al. |
| 2005/0073742 | A1 | 4/2005 | Weyh et al. |

(Continued)

FOREIGN PATENT DOCUMENTS

| | | |
|---|---|---|
| JP | 2011191199 A | 9/2011 |
| WO | 2014099959 A1 | 6/2014 |

OTHER PUBLICATIONS

U.S. Appl. No. 14/511,810, filed Oct. 10, 2014—Title: Compressive Sensing for Metrology (Not yet published).

*Primary Examiner* — Tarifur Chowdhury
*Assistant Examiner* — Md M Rahman
(74) *Attorney, Agent, or Firm* — Suiter Swantz pc llo (57) ABSTRACT

Methods and systems are provided, which pattern an illumination of a metrology target with respect to spectral ranges and/or polarizations, illuminate a metrology target by the patterned illumination, and measure radiation scattered from the target by directing, at a pupil plane, selected pupil plane pixels from a to respective single detector(s) by applying a collection pattern to the pupil plane pixels. Single detector measurements (compressive sensing) has increased light sensitivity which is utilized to pattern the illumination and further enhance the information content of detected scattered radiation with respect to predefined metrology parameters.

10 Claims, 6 Drawing Sheets

(51) Int. Cl.
*G01N 21/95* (2006.01)
*G01N 21/47* (2006.01)

(56) References Cited

U.S. PATENT DOCUMENTS

| | | | |
|---|---|---|---|
| 2005/0168790 A1* | 8/2005 | Latypov | G03F 7/70291 359/239 |
| 2006/0239336 A1* | 10/2006 | Baraniuk | H04L 25/20 375/216 |
| 2007/0279636 A1 | 12/2007 | Li et al. | |
| 2008/0018874 A1* | 1/2008 | Dusa | G03F 7/70516 355/55 |
| 2010/0314554 A1 | 12/2010 | Galimberti et al. | |
| 2012/0069342 A1* | 3/2012 | Dalgleish | G01N 21/47 356/445 |
| 2012/0327503 A1* | 12/2012 | Manassen | G01J 1/4257 359/291 |
| 2013/0321810 A1* | 12/2013 | Wang | G01N 21/211 356/369 |
| 2014/0168650 A1* | 6/2014 | Manassen | G01N 21/55 356/432 |
| 2014/0307245 A1* | 10/2014 | Tanaka | G03F 7/70566 355/71 |

\* cited by examiner

```
410 — PATTERNING A TARGET ILLUMINATION
       WITH RESPECT TO ITS SPECTRAL
       RANGE AND/OR POLARIZATION

412 — CARRYING OUT THE PATTERNING IN
       A PUPIL PLANE OF THE ILLUMINATION

415 — PATTERNING THE TARGET ILLUMINATION
       WITH RESPECT TO BOTH ITS SPECTRAL
       RANGE AND ITS POLARIZATION

417 — PATTERNING THE TARGET ILLUMINATION WITH
       RESPECT TO ITS SPECTRAL RANGE BY A
       SPECTRUM PROGRAMMER

420 — ILLUMINATING A METROLOGY TARGET
       BY THE PATTERNED ILLUMINATION

430 — MEASURING RADIATION SCATTERED
       FROM THE TARGET

435 — APPLYING A COLLECTION PATTERN
       TO THE PUPIL PLANE IMAGE
```

COMPRESSIVE SENSING WITH ILLUMINATION PATTERNING

CROSS REFERENCE TO RELATED APPLICATIONS

This application is filed under 35 U.S.C. §120 and §365(c) as a continuation of International Patent application Ser. No. PCT/US15/21843, filed on Mar. 20, 2015, which application claims the benefit under 35 U.S.C. 119(e) of U.S. Provisional Patent Application No. 61/955,793 filed on Mar. 20, 2014, which applications are incorporated herein by reference in their entirety.

FIELD OF THE INVENTION

The present invention relates to the field of metrology, and more particularly, to using illumination patterning and pupil sampling to enhance measurement accuracies.

BACKGROUND OF THE INVENTION

Metrology faces an ever growing challenge of improving the accuracy of continuously shrinking device structures and thus strives to enhance the information content of metrology measurements. Manipulations of illumination and of detection schemes are key features in improving metrology performance.

BRIEF SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a method comprising patterning an illumination of a metrology target with respect to at least one of a spectral range thereof and a polarization thereof, and measuring radiation scattered from the illuminated target by collecting, from a pupil plane, selected pupil plane pixels to respective at least one single detector by applying a collection pattern to the pixels of the pupil plane image.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Prior to the detailed description being set forth, it may be helpful to set forth definitions of certain terms that will be used hereinafter.

The terms "patterning" or "coding" as used in this application to refer to a pixel-related definition of an optical parameter at the pupil plane of an optical system. For example, spectral parameters or polarization may be handled with respect to the pixel location at any of the system's pupil planes.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Methods and systems are provided, which pattern an illumination pupil with respect to spectral ranges and/or polarizations, illuminate a metrology target by the patterned illumination, and measure radiation scattered from the target by directing, at a pupil plane, selected pupil plane pixels to respective single detector(s) by applying a collection pattern to the pupil plane pixels. Single detector measurements (compressive sensing) are utilized to maintain sensitivity when illumination levels are decreased due to losses from illumination patterning and to further enhance the information content of detected scattered radiation with respect to predefined metrology parameters. The illumination parameters (e.g., spectrum, polarization) may be analytically optimized, e.g., by principal component analysis (PCA). By controlling all photon degrees of freedom, namely, angle (position at the pupil plane, i.e., pixel), wavelength and polarization, it is possible to illuminate the metrology target with only photons carrying correlative information for the measurement (as explained below) and thus enhance its precision and sensitivity.

Figure 1:
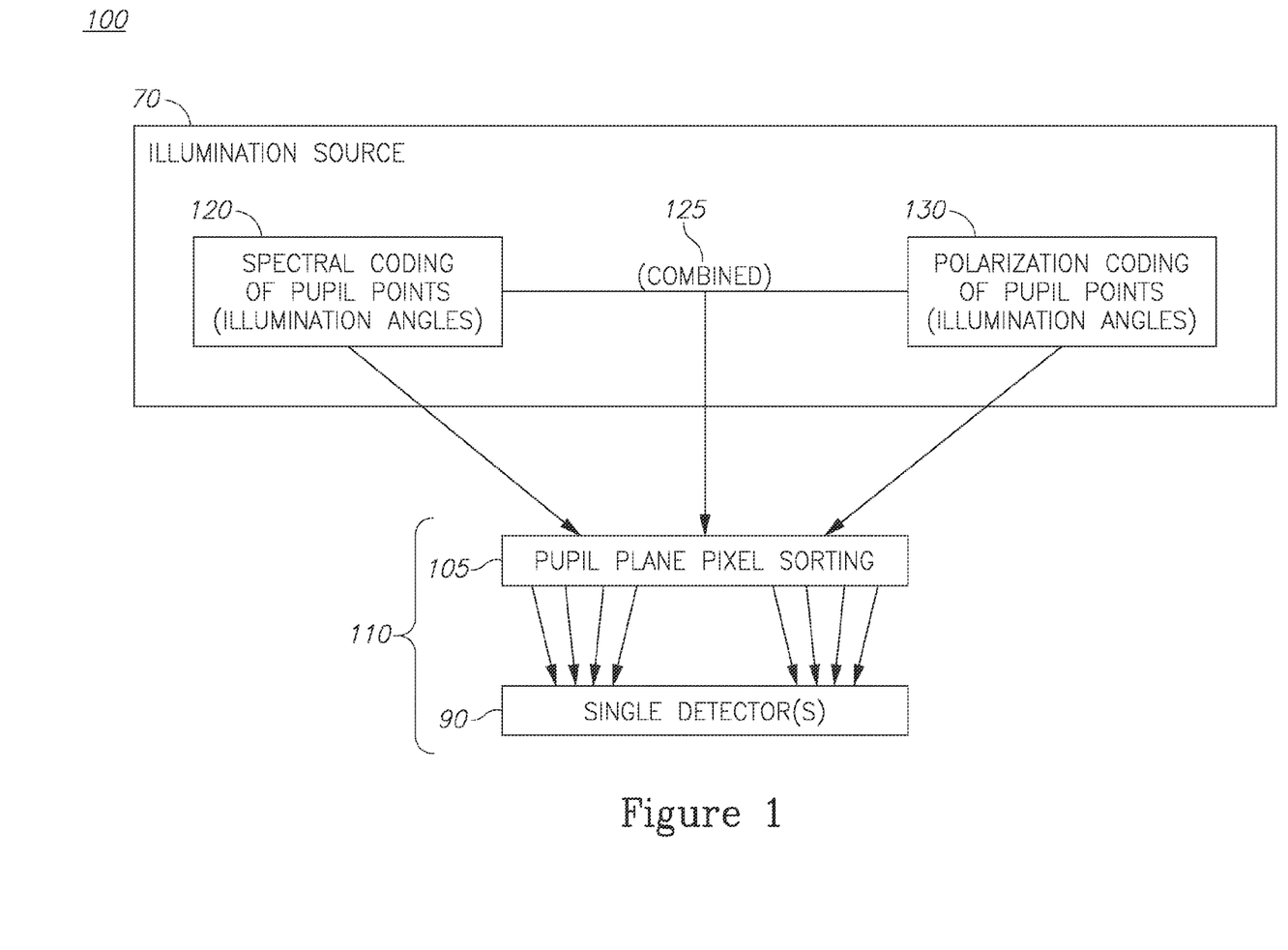
FIG. 1 is a high level schematic block diagram of a metrology optical system, according to some embodiments of the invention.

FIG. 1 is a high level schematic block diagram of a metrology optical system 100, according to some embodiments of the invention. FIG. 1 is highly schematic and illustrates conceptual configurations of system 100 which are described in more detail below. Metrology optical system 100 comprises an illumination source 70 configured to pattern a target illumination with respect to at least one of a spectral range thereof and a polarization thereof, and a compressive sensing device 110 configured to measure radiation scattered from a target illuminated by the patterned illumination, by directing, at a pupil plane, selected pupil plane pixels to respective at least one single detector 90 of the device by applying a collection pattern for pupil plane pixel sorting 105 to the pupil plane pixels. At illumination source 70, spectral coding 120 of pupil points (which constitute illumination angles upon the target at the field plane), polarization coding 130 thereof or both spectral and polarization coding 125 of the target illumination may be carried out.

Embodiments of the invention use patterned illumination with respect to spectrum, polarization and/or location on the pupil plane (i.e., illumination angle) to increase the content of metrology information extracted from the target measurement. The resulting severe light budget constraints are resolved by pre-preparing the spectral and/or polarization pupil states along with the intensity pupil states according to an analysis of the sensitivity to the measured quantity in methods such as principal components analysis (PCA). The light prepared in the designed states is scattered off the target and measured with single detector(s) to reduce noise and thus enhance the sensitivity to enable measurements of the patterned illumination. Compressive sensing is used to overcome low light levels by analyzing the sensitivity of the different pupil pixels to a metrology quantity and allowing only pixels that have correlated behavior to participate in the measurement. In certain embodiments, controllable mirror devices placed at the pupil plane are used to shape the collection function to include only pixels that behave in a correlated way with changing value of the measured parameter. The reflected photons are then focused onto a single detector. Different patterns may be used to feed multiple single detectors. For example, in a SCOL (scatterometry overlay) measurement, pixels that behave correlatively in response to an intentional overlay may be reflected into the single detector. Then, the different cells having different intentional overlay values, are measured and instead of pupil images, detector readings are collected. This procedure may be repeated for additional sets of correlated pixels. Advantageously, this method avoids the readout noise of the pupil image sensor pixels and suffers only from the readout noise of a single detector. Collecting more photons on a single detector is also beneficial in terms of shot noise. This improved SNR (signal to noise ratio) is used to enable patterning of the illumination at the pupil plane that allows deriving additional information from the measurement. Systems that implement the sensing principle described above are termed herein "compressive sensing" systems.

Figure 2:
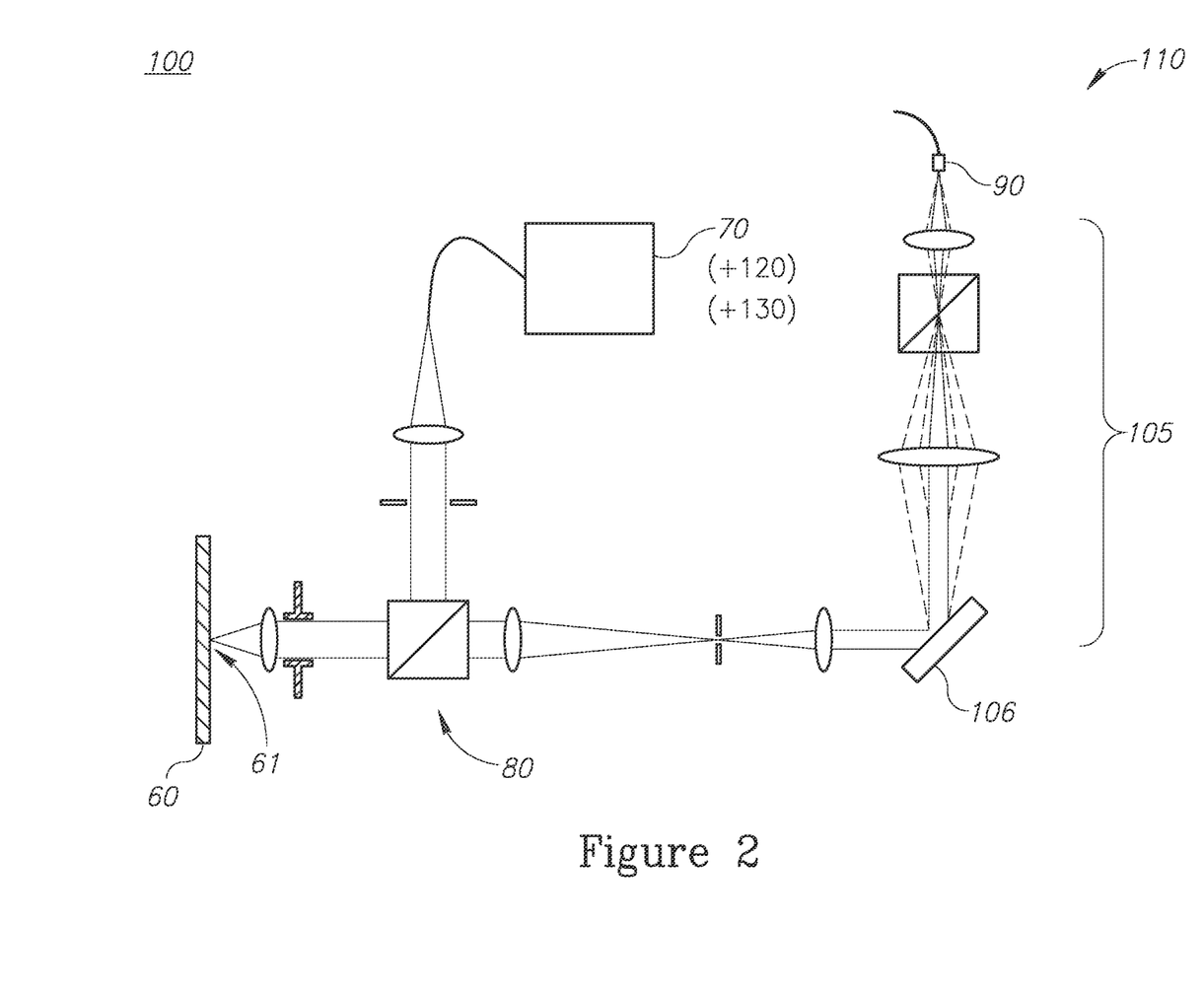
FIG. 2 is a high level schematic illustration of a metrology optical system with a pixelated pupil plane sampling configuration, according to some embodiments of the invention.
Figure 3:
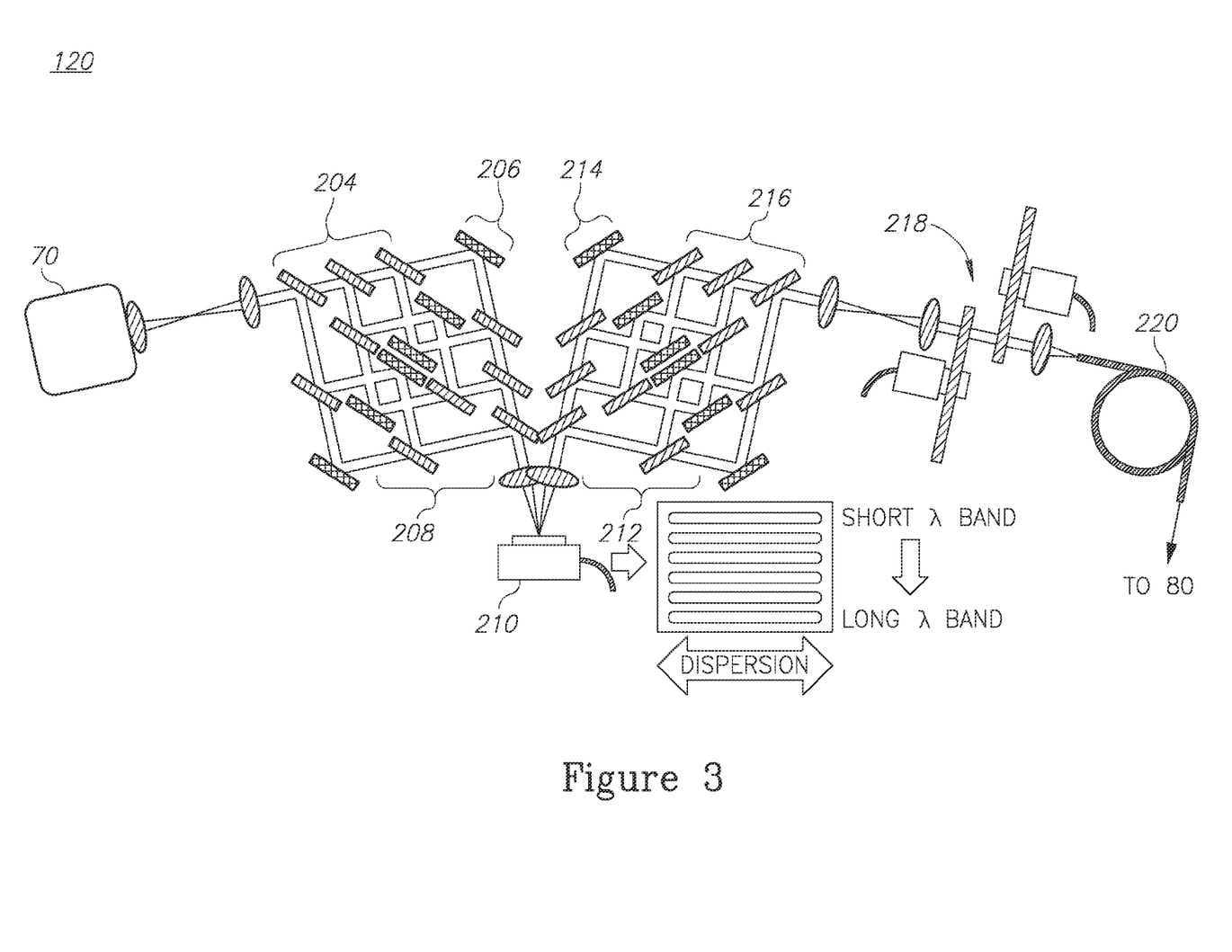
FIG. 3 is a high level schematic illustration of a spectrum programmer for spectral coding, according to some embodiments of the invention.
Figure 4:
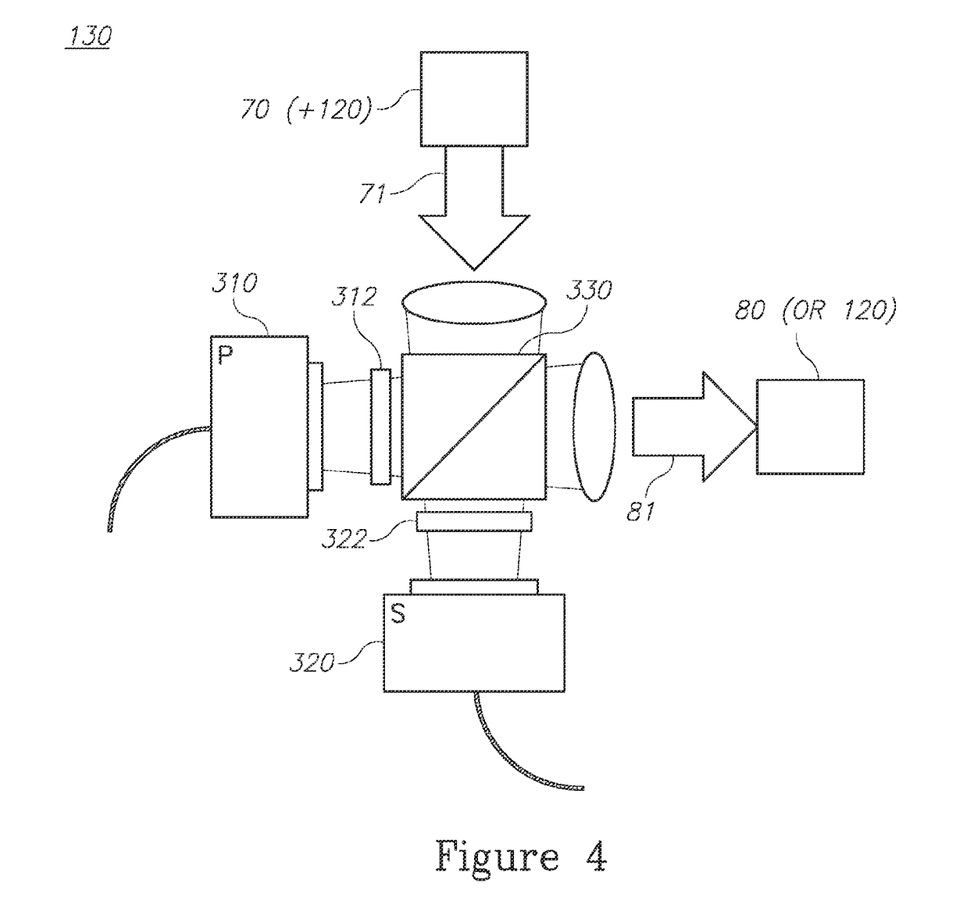
FIG. 4 illustrates schematically a polarization programmer configured to pattern the target illumination with respect to its polarization, according to some embodiments of the invention; and, FIG. 5 is a high level flowchart illustrating a method, according to some embodiments of the invention.

FIGS. 2-4 are schematic representations of system 100 and its elements, according to some embodiments of the invention. FIG. 2 is a high level schematic illustration of metrology optical system 100 with a pixelated pupil plane sampling configuration 105, according to some embodiments of the invention. FIG. 3 is a high level schematic illustration of a spectrum programmer for spectral coding 120, according to some embodiments of the invention. FIG. 3 is a high level schematic illustration of a polarization coding configuration 130, according to some embodiments of the invention.

FIG. 2 schematically illustrates illumination source 70 with spectral patterning 120 and/or polarization patterning 130 illuminating via an optical configuration 80 of lenses, apertures and beam splitter(s) (possibly at least partly carried out using optical fibers) a target 61 on a wafer 60, from which scattered radiation (e.g., reflected diffraction orders) is directed via optical configuration 80 to compressive sensing device 110. The latter is schematically illustrated, in a non-limiting manner, as having a controllable mirror device 106 (e.g., a DMD—digital micro-mirror device used in DLP—digital light processing technology) that directs the scattered radiation, using a collection pattern to single detector(s) 90 to reduce the noise level of the signal and hence increase its sensitivity to low levels of illumination which result from applying the spectral and/or polarization patterning. U.S. patent application Ser. No. 14/511,810, which is incorporated herein by reference in its entirety, teaches further details concerning compressive sensing device 110 which may be applied to the presently disclosed systems and methods.

Certain embodiments, e.g., ones applying spectral or polarization patterning as explained below, eliminate a prior art need to couple the light scattered from the DLP, used for angular pupil states selection, into a spectrometer fiber and thus avoid the spectral diffraction difficulties associated with such a coupling. Certain embodiments eliminate a prior art need to scan the source wavelength with a monochromator and thus avoid the severe measurement time penalty associated with such a scan. Compressive sensing device 110, by improving low light SNR (signal to noise ratio), enables the flexible control of the system's degrees of freedom without using broadband illumination required for prior art systems.

FIG. 3 illustrates schematically a spectrum programmer 120 configured to pattern the target illumination with respect to the spectral range, according to some embodiments of the invention. Spectrum programmer 120 is an exemplary embodiment configured to provide spectral patterning 120, which is described in detail in WIPO Publication No. 2014099959. Spectrum programmer 120 is configured to divide illumination range 70 (e.g., white light) to distinct bands, using dichroic filters 204, 206, 208, 212, 214 and 216 with further diffraction by diffraction gratings 210 as explained below. In embodiments described in FIG. 2, the dispersed light may be dispersed over the area of controllable mirror device 106, programmed to determine the output spectrum. Embodiments of spectrum programmer 120 may reach a resolution of 10 nm, are more effective than wavelength scanning and solve fiber coupling sensitivities and measurement speed penalties of prior art methods.

As described in WIPO Publication No. 2014099959, which is incorporated herein by reference in its entirety, spectral control system 120 (also termed spectrum programmer 120) comprises multiple sub-dispersion paths and sub-combination paths to enable wider spread of illumination spectra. Broadband illumination delivered along the dispersion path by illumination source 70 may be split into a selected number of portions, each within a respective spectral band. Then each portion may be dispersed into a plurality of dispersed portions forming a plurality of spectral continuums (denoted by the range short λ band to long λ band schematically illustrated next to dispersion grating 210) for higher resolution control of the illumination spectra. For example, illumination may be split among six sub-dispersion paths leading to six respective dispersive elements 206 for as much as six times the resolution attainable with a single-line dispersion path. The foregoing example is illustrative of the increased resolution of spectral control attainable with multi-path dispersion. It is noted, however, that the number of sub-paths is arbitrary and no limitation is intended by the illustrative examples provided herein. In some embodiments, the dispersion path may include a first plurality of dichroic splitters 204 configured to receive illumination directed along the dispersion path from illumination source 202. Dichroic splitters 204 may be further configured to direct portions illumination within specified spectral bands or ranges along sub-dispersion paths leading to the respective dispersive elements 206. For example, dichroic splitters 206 may be configured to divide illumination received from illumination source 202 into a plurality of bands within the range of 300 to 900 nm. The dispersion path may further include a second plurality of dichroic splitters 208 configured to direct the dispersed portions of illumination from each sub-dispersion path along a common path to at least one spectral controller 210. Dispersed portions of illumination from each sub-path directed onto a surface of spectral controller 210. By dividing the illumination into a plurality of portions within respective spectral bands and then dispersing each portion into a spread out spectral continuum, spectral controller 210 is arranged to exclude selected portions within each of the plurality of spectral bands. Since the illumination is spread over a greater surface (e.g., six times as much surface area) of spectral controller 210, spectral controller 210 is arranged to control the excluded/transmitted selection of illumination spectra with improved resolution due to the increased number of array elements that can be activated/deactivated to affect illumination spectra. Higher resolution without undue cost and system complexity may be achieved by separating illumination into multiple strips directed at a single spatial light modulator. Furthermore, recombining the spectrally controlled illumination along a common illumination path preserves spectral brightness of the illumination source 202. The combination path may include a reversed configuration of elements that mirrors the dispersion path. For example, the combination path may include a first plurality of dichroic combiners 212 configured to direct transmitted portions of dispersed illumination from spectral controller 210 along a plurality of sub-combination paths leading to respective combination elements 214. The combination path may further include a second plurality of dichroic combiners 216 configured to direct the substantially coaxial (undispersed) illumination received from each combination element 214 (i.e., each sub-combination path) onto a common illumination path. In some embodiments, the illumination path may further include one or more neutral density filters 218 configured to control an intensity level of the spectrally controlled illumination. As discussed above, the illumination path may be delineated by any number of optical elements, such as an optical fiber 220 configured to deliver at least a portion of spectrally controlled illumination to optical configuration 80. It is noted that the terms "dichroic splitter" and "dichroic combiner" may be interchangeably utilized to reference an illumination splitting or combining functionality. However, the term "dichroic splitter" is generally used herein to refer to a dichroic splitter/combiner disposed along the dispersive path, and the term "dichroic combiner" is generally used herein to refer to a dichroic splitter/combiner disposed along the combination path. Accordingly, the use of either term should not be understood to limit the disclosure in any way.

FIG. 4 illustrates schematically a polarization programmer 130 configured to pattern the target illumination with respect to its polarization, according to some embodiments of the invention. Non-polarized illumination 70 (supported by spectral programming 120) enters (71) via a lens and polarizing beam splitter 330 which splits it to two components, e.g. s and p polarization components. The components pass through λ/4 waveplates 312, 322 and are reflected by respective p- and s-mirror arrays 310, 320, to yield circularly polarized light 81. DLP p- and s-mirror arrays 310, 320 are positioned at illumination pupil conjugates to provide independent reflectance programming for both p- and s-polarization. The reflected light from mirror arrays 310, 320 is changed back to rotated linear with λ/4 waveplates 312, 322 (respectively) and both polarizations are recombined in beam splitter 330 to form polarization structured light 81. Polarization programmer 130 may be configured to control both the polarization pattern and the intensity pattern across the pupil plane.

In certain embodiments, system 100 creates correlative angle (pupil plane pixel position)-wavelength-polarization groups by corresponding patterning at the pupil plane, to yield pixel correlations that are used to direct specified pixels to he sensed by single detectors. System 100 may employ patterning and respective grouping according to any illumination parameter.

Figure 5:
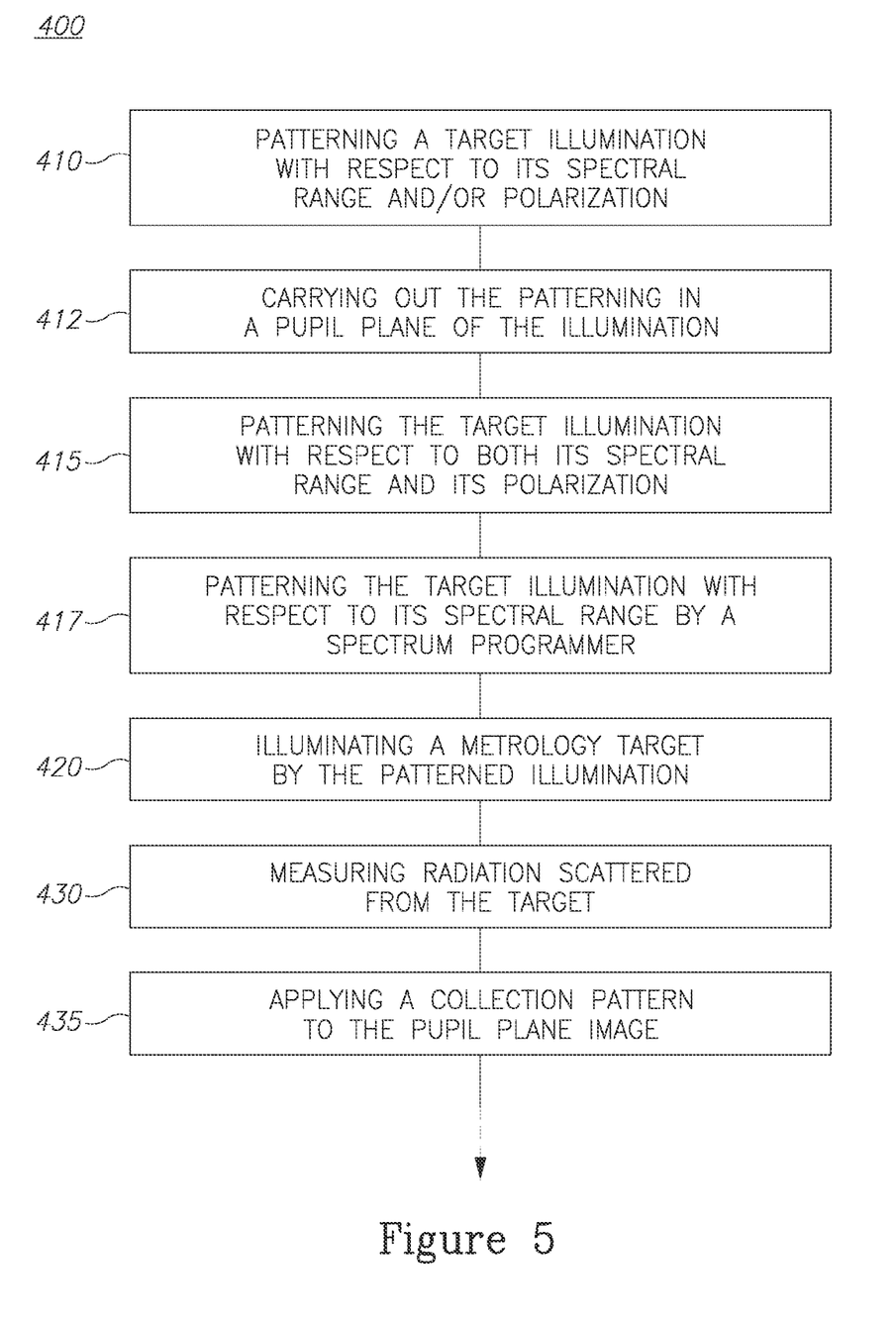

FIG. 5 is a high level flowchart illustrating a method 400, according to some embodiments of the invention. Method 400 comprises patterning a target illumination with respect to its spectral range and/or polarization (stage 410), illuminating a metrology target by the patterned illumination (stage 420) and measuring radiation scattered from the target (stage 430) by directing, at a pupil plane, selected pupil plane pixels to respective single detector(s) (stage 440) which is carried out by applying a collection pattern to the pupil plane pixels (stage 435).

In certain embodiments, method 400 may further comprise carrying out the patterning in a pupil plane of the illumination (stage 412), patterning the target illumination with respect to both its spectral range and its polarization (stage 415) and/or patterning the target illumination with respect to its spectral range by a spectrum programmer (stage 417). Method 400 may further comprise relating the collection pattern to the illumination patterning (stage 437).

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method comprising:
pre-preparing at least one of a spectral pupil state or polarization pupil state and an intensity pupil state according to an analysis of a sensitivity to a measured quantity using principal components analysis;
patterning an illumination of a metrology target with respect to at least one of a spectral range thereof and a polarization thereof to create a patterned illumination;
illuminating the metrology target by the patterned illumination; and,
measuring radiation scattered from the metrology target by directing, at a pupil plane, selected pupil plane pixels to a plurality of single detectors by shaping a first collection function with one or more controllable mirror devices placed at the pupil plane to include only pixels correlated to a first intentional overlay, and shaping a second collection function to include only pixels correlated to a second intentional overlay, the first intentional overlay and second intentional overlay having different overlay values.

2. The method of claim 1, wherein the step of patterning is carried out in a pupil plane of the illumination.

3. The method of claim 1, wherein the collection pattern is configured to relate to a pattern of the patterned illumination.

4. The method of claim 1, wherein the illumination of the metrology target is patterned with respect to both the spectral range and the polarization thereof.

5. The method of claim 1, wherein the illumination of the metrology target is patterned with respect to the spectral range by a spectrum programmer.

6. A metrology optical system comprising:
an illumination source configured to pattern a target illumination with respect to at least one of a spectral range thereof and a polarization thereof to create a patterned illumination; and,
a compressive sensing device configured to measure radiation scattered from the target illuminated by the patterned illumination by directing, at a pupil plane, selected pupil plane pixels to a plurality of single detectors of the compressive sensing device by shaping a first collection function with one or more controllable mirror devices placed at the pupil plane to include only pixels correlated to a first intentional overlay, and shaping a second collection function to include only pixels correlated to a second intentional overlay, the first intentional overlay and second intentional overlay having different overlay values, wherein at least one of a spectral pupil state or polarization pupil state and an intensity pupil state are pre-prepared according to an analysis of a sensitivity to a measured quantity using principal components analysis.

7. The metrology optical system of claim 6, wherein the patterning is carried out in a pupil plane of the illumination source.

8. The metrology optical system of claim 6, wherein the collection pattern is configured to relate to a pattern of the patterned illumination.

9. The metrology optical system of claim 6, wherein the target illumination is patterned with respect to both the spectral range and the polarization thereof.

10. The metrology optical system of claim 6, further comprising:
a spectrum programmer comprising multiple sub-dispersion paths and sub-combination paths, which is configured to pattern the target illumination with respect to the spectral range.

* * * * *